United States Patent
Herbelin et al.

(10) Patent No.: US 12,145,984 B2
(45) Date of Patent: Nov. 19, 2024

(54) METHODS FOR PREVENTING ISCHEMIA REPERFUSION INJURY IN AN ORGAN WITH ANTIBODY ANTAGONISTS OF IL-33

(71) Applicants: INSERM (INSTITUT NATIONAL DE LA SANTÉ ET DE LA RECHERCHE MÉDICALE), Paris (FR); UNIVERSITÉ DE POITIERS, Poitiers (FR); CENTRE HOSPITALIER UNIVERSITAIRE DE POITIERS, Poitiers (FR); CENTRE NATIONAL DE LA RECHERCHE SCIENTIFIQUE (CNRS), Paris (FR)

(72) Inventors: André Herbelin, Poitiers (FR); Jean-Marc Gombert, Poitiers (FR); Maroua Ferhat, Salt Lake City, UT (US); Antoine Thierry, Poitiers (FR); Jean-Philippe Girard, Toulouse (FR)

(73) Assignees: INSTITUT NATIONAL DE LA SANTE ET DE LA RECHERCHE MEDICALE (INSERM), Paris (FR); CENTRE HOSPITALIER UNIVERSITAIRE DE POITIERS, Poiters (FR); UNIVERSITE DE POITIERS, Poiters (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/964,785

(22) PCT Filed: Jan. 24, 2019

(86) PCT No.: PCT/EP2019/051738
§ 371 (c)(1),
(2) Date: Jul. 24, 2020

(87) PCT Pub. No.: WO2019/145413
PCT Pub. Date: Aug. 1, 2019

(65) Prior Publication Data
US 2021/0054064 A1 Feb. 25, 2021

(30) Foreign Application Priority Data
Jan. 24, 2018 (EP) .................................... 18305054

(51) Int. Cl.
*A61K 39/395* (2006.01)
*A61K 38/17* (2006.01)
*A61P 13/12* (2006.01)
*C07K 16/24* (2006.01)
*C12N 15/113* (2010.01)
*A61K 39/00* (2006.01)
*A61P 9/10* (2006.01)
*C07K 14/54* (2006.01)
*C07K 16/28* (2006.01)

(52) U.S. Cl.
CPC ........ *C07K 16/244* (2013.01); *A61K 38/1793* (2013.01); *A61K 39/3955* (2013.01); *A61P 13/12* (2018.01); *C12N 15/1136* (2013.01); *A61K 2039/505* (2013.01); *A61P 9/10* (2018.01); *C07K 14/54* (2013.01); *C07K 16/2866* (2013.01); *C07K 2317/76* (2013.01); *C07K 2319/30* (2013.01); *C12N 2310/11* (2013.01); *C12N 2310/14* (2013.01)

(58) Field of Classification Search
CPC ..... C07K 16/244; A61K 39/3955; A61P 9/10; A61P 13/12
See application file for complete search history.

(56) References Cited

U.S. PATENT DOCUMENTS

2016/0289322 A1* 10/2016 Fujino .................. C07K 16/244

FOREIGN PATENT DOCUMENTS

WO 2008/132709 A1 6/2008

OTHER PUBLICATIONS

Chen et al, 2018 (Cell Physiol Biochem. 49: 349-358, published online Aug. 23, 2018).*
Liang et al (2017. European Journal of Pharmacology. 812: 18-27; available online Jun. 29, 2017).*
Hosten, "BUN and Creatinine", Chapter 193 (pp. 874-878) of Clinical Methods: The History, Physical, and Laboratory Examination, 3rd Edition. Published by Butterworths, 1990.*
Park et al (2016. Int Neurourol J. 20: 114-121).*
Akcay et al: "IL-33 Exacerbates Acute Kidney Injury", Journal of the Amercian Society of Nephrology, vol. 22, No. 11, pp. 2057-2067, Nov. 2011.

(Continued)

Primary Examiner — Zachary C Howard
(74) Attorney, Agent, or Firm — WC&F IP

(57) ABSTRACT

Inflammation is a prominent feature of ischemia-reperfusion injury (IRI) characterized by leukocyte infiltration and renal tubular injury. However, the signals that initiate these events remain poorly understood. The inventors identify the nuclear alarmin interleukin (IL)-33 as an initiation factor of tissue injury and also as a major amplification factor of the innate immune response triggered by experimental kidney ischemia-reperfusion in mice. In mice lacking IL-33, IRI is reduced, as attested by early decreased tubular cell injury, and by subsequent decreased infiltration of IFN-γ/IL-17A-producing neutrophils and preservation of renal functions. These findings led the inventors to propose that endogenous IFN-33 contributes to kidney IRI by promoting iNKT cell recruitment and cytokine production, resulting in neutrophil infiltration and activation at the injury site. Accordingly, the present invention relates to antagonists of IL-33 for use in methods for preventing ischemia reperfusion injury in an organ.

7 Claims, 4 Drawing Sheets

(56) References Cited

OTHER PUBLICATIONS

Figure 1A:
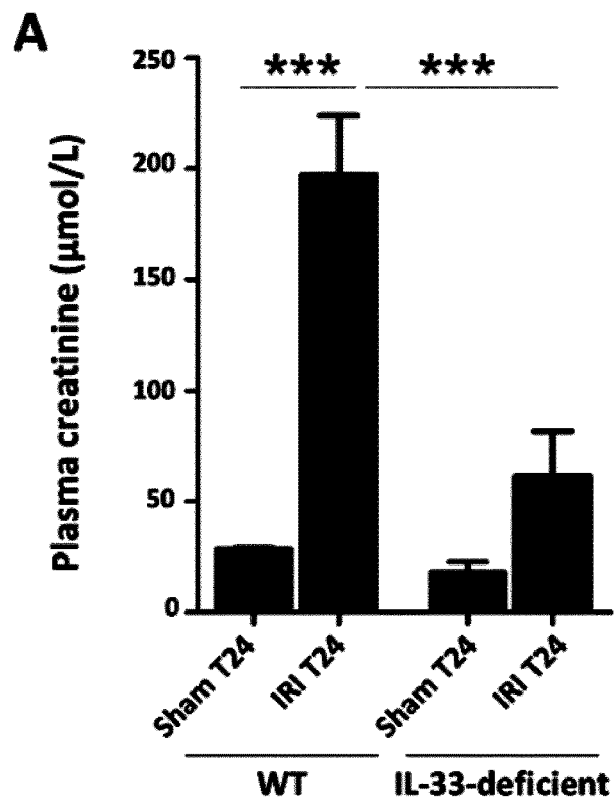
Figure 1B:
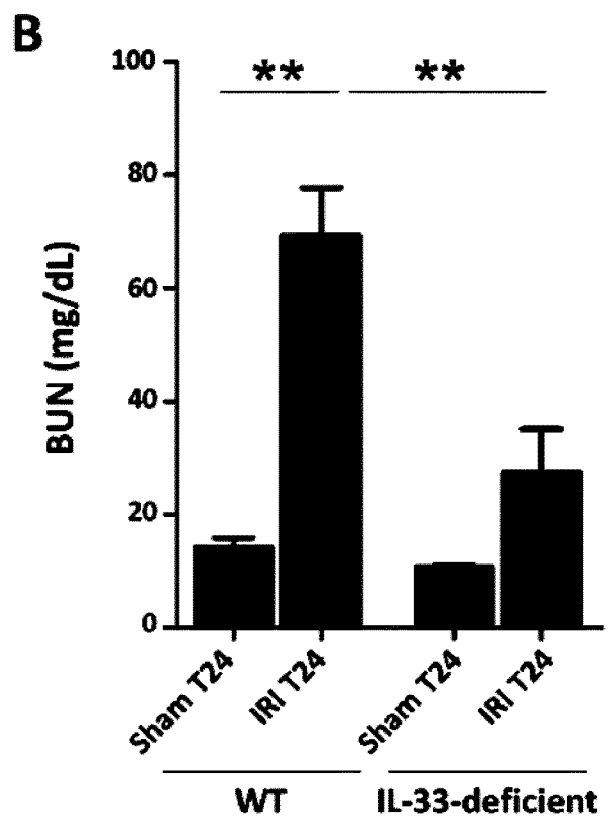

Bao et al: :Characterization of Interleukin-33 and Soluble ST2 in Serum and Their Association with Disease Severity In Patients with Chronic Kidney Disease, Journal of Clinical Immunology, vol. 32, No. 3, pp. 587-594, Dec. 28, 2011.
Fagundes et al: "ST2, an IL-1R family member, attenuates inflammation and lethality after intestinal ischemia and reperfusion", Journal of Leukosyte Biology, vol. 81, No. 2, pp. 492-499, Feb. 2007.
Ferhat et al: "Renal IL-33 induces $Cell/Neutrophil infiltration and exacerbates kidney ishcemia-reperfusion-induced injury", Transplant International Sep. 1, 2017 Blackwell Publishing Ltd NLD, vol. 30, No. Supplement 2, Sep. 1, 2017.
Gombert et al: "Study of alarmin release during ishemia reperfusion injury after human renal transplantation", Journal of Immunology, vol. 190, May 2013.
Yin et al: "Pretreatment with soluble ST2 reduces warm hepatic ischemia/reperfusion injury", Biochemical and Biophysical Research, vol. 351, No. 4, pp. 940-946, Dec. 29, 2006.

\* cited by examiner

METHODS FOR PREVENTING ISCHEMIA REPERFUSION INJURY IN AN ORGAN WITH ANTIBODY ANTAGONISTS OF IL-33

FIELD OF THE INVENTION

The present invention relates to antagonists of IL-33 for use in methods for preventing ischemia reperfusion injury in an organ.

BACKGROUND OF THE INVENTION:

Ischemia-reperfusion injury (IRI) upon renal transplantation contributes to graft damage[1] after a complex pathophysiology involving mitochondrial dysfunction, release of reactive oxygen species, cellular necrosis, apoptosis and tissue damage. It results in impaired organ function[2], leading to fibrosis[3].

Studies in IRI models have demonstrated that inflammatory responses mediated by the innate immune system cause renal damage[2-6]. However, the mechanisms of early activation and recruitment of immune cells to the post-ischemic kidney are still unclear, raising the question of possible involvement of proinflammatory damage-associated molecular patterns (DAMPs), which are host biomolecules that can initiate a noninfectious inflammatory response[7-8]. DAMPs are normally intracellular, shielded from the immune system by plasma membranes[9-10], and their release, following tissue injury, signals cellular damage and activates the innate immune system[9-12]. A subset of DAMPs, called alarmins, are tissue-derived nuclear proteins, which are constitutively expressed at high levels in epithelial barrier tissues and endothelial barriers. These potent immunostimulants, which include defensins, cathelicidin, eosinophil-derived neurotoxin, high-mobility group box protein 1, and interleukin (IL)-1α, have the capacity to activate Toll-like receptors (TLR) or cytokine receptors, and serve as early warning signals to alert adjacent cells/tissues and to mobilize innate and adaptive immune systems[13].

Important pro-inflammatory functions have also been ascribed to IL-33, both as conventional cytokine and as an alarmin[14-19]. IL-33, initially identified as a nuclear factor called NF-HEV[20] (for "Nuclear Factor of High-Endothelial Venules"), is the most recent member of the IL-1 receptor superfamily of cytokines which also comprises IL-1-β and IL-18. It is constitutively expressed by various tissues, including kidney, in the nucleus of endothelial and epithelial cells and/or fibroblasts[14-19,21]. During tissue stress resulting from infection or trauma, IL-33 is released by necrotic cells as alarmin and rapidly targets both non-immune and innate immune cells, thereby increasing proinflammatory cytokine secretion[18,19,22]. Upon binding to its specific receptor ST2 and co-receptor IL-1 receptor accessory protein (IL-1RAcP)[14,15], IL-33 initiates the MyD88 (Myeloid differentiation primary response gene 88)-dependent inflammatory pathway. IL-33 can be negatively regulated by sST2 (soluble ST2), which acts as a decoy receptor for IL-33[19].

IL-33 has been described as a potent inflammatory mediator with deleterious effects in nephrotoxic and obstructive AKI[21,23]. However, in the two models, early alarmin-like release of IL-33 has not been documented, since IL-33 is apparently synthetized within 2-4 days after AKI induction, like a conventional cytokine. On the other hand, the protective effects of exogenous IL-33 through activation of ST2-expressing counter-regulatory immune cells such as type 2 innate lymphoid cells[24] and Treg[25] have been documented in some experimental AKI settings.

In humans, IL-33 has been implicated in chronic kidney diseases[26,27]. Regarding renal transplantation, our recent findings suggest that during kidney IRI, IL-33 acts as an alarmin promptly released into serum and urine after reperfusion[28]. In this clinical situation, IL-33 levels and IRI duration are correlated, supporting a close connection between kidney cell injury and IL-33 release[28]. Nonetheless, direct proof of the involvement of IL-33 in experimental kidney IRI has not been provided so far.

SUMMARY OF THE INVENTION

The present invention relates to antagonists of IL-33 for use in methods for preventing ischemia reperfusion injury in an organ. In particular, the present invention is defined by the claims.

DETAILED DESCRIPTION OF THE INVENTION

Inflammation is a prominent feature of ischemia-reperfusion injury (IRI) characterized by leukocyte infiltration and renal tubular injury. However, the signals that initiate these events remain poorly understood. The present study identifies the nuclear alarmin interleukin (IL)-33 as an initiation factor of tissue injury and also as a major amplification factor of the innate immune response triggered by experimental kidney ischemia-reperfusion in mice. IL-33 is constitutively expressed throughout the kidney in peritubular and periglomerular spaces, mainly by microvascular endothelial cells, from which it is released immediately during IRI. In mice lacking IL-33 (IL-33Gt/Gt), IRI is reduced, as attested by early decreased tubular cell injury, and by subsequent decreased infiltration of IFN-γ/IL-17A-producing neutrophils and preservation of renal functions. This protection is associated with a decrease of myeloid DC, NK and iNKT cells, which are known for their potentially deleterious role in IRI. Increase of circulating IL-12, a key IL-33 co-player, and surface IL-33 specific receptor overexpression on iNKT cells precede the IL-33- and iNKT cell-dependent phase of neutrophil cell infiltration. This finding, along with the in vitro observation that IL-33 targets iNKT cells by inducing both IFN-γ and IL-17A led the inventors to propose that endogenous IL-33 contributes to kidney IRI by promoting iNKT cell recruitment and cytokine production, resulting in neutrophil infiltration and activation at the injury site. Taken together, inventors' findings demonstrate a novel molecular mediator contributing to innate immune cell recruitment induced by renal ischemia-reperfusion and may provide new therapeutic insights into acute kidney injury associated with renal transplantation.

Accordingly the first object of the present invention relates to a method of preventing, reducing the severity of, or reducing the risk of ischemia reperfusion injury in an organ comprising administering to the organ a therapeutically effective amount of an IL-33 antagonist.

As used herein, the term "ischemia" as used herein refers to a restriction in blood supply with resultant damage or dysfunction of the organ. Rather than hypoxia (a more general term denoting a shortage of oxygen, usually a result of lack of oxygen in the air being breathed), ischemia is an absolute or relative shortage of the blood supply to an organ, i.e. a shortage of oxygen, glucose and other blood-borne components. A relative shortage means the mismatch of blood supply (oxygen/fuel delivery) and blood request for adequate metabolism of tissue. Ischemia can also be described as an inadequate flow of blood to a part of the body, caused by constriction or blockage of the blood vessels supplying it. This can be due to, but is not limited to, such as hypoglycemia (lower than normal level of blood glucose); tachycardia (abnormally rapid beating of the heart); atherosclerosis (lipid-laden plaques obstructing the lumen of arteries); hypotension (low blood pressure, e.g. in septic shock, heart failure); thromboembolism (blood clots); outside compression of a blood vessel, e.g. mechanically by pressure, severing of a blood vessel, implantation of a transplanted organ, surgery, by a tumor, and the like; embolism (foreign bodies in the circulation, e.g. amniotic fluid embolism); sickle cell disease (abnormally shaped red blood cells); induced g-forces which restrict the blood flow and force the blood to the extremities of the body, as in acrobatics and military flying; and localized extreme cold, such as by frostbite, ice, or improper cold compression therapy.

As used herein, the term "reperfusion" has its general meaning in the art and refers to the restoration of blood flow to a tissue following ischemia.

Accordingly, the term "ischemia reperfusion" is thus intended to encompass an event wherein an episode of ischemia is followed by an episode of reperfusion and the term "ischemia reperfusion injury" refers to the tissue damage caused by an ischemia reperfusion event. The absence of oxygen and nutrients from blood during the ischemic period creates a condition in which the restoration of circulation results in inflammation and oxidative damage through the induction of oxidative stress rather than (or along with) restoration of normal function.

The method of the present invention is particularly suitable for preventing fibrosis and organ dysfunction. As used herein, the term "fibrosis" refers to the formation of fibrous tissue as a reparative or reactive process, rather than as a normal constituent of an organ or tissue.

Fibrosis is characterized by myofibroblast accumulation and collagen deposition in excess of normal deposition in any particular tissue. As used herein, the term "organ dysfunction" means and includes a reduction or impairment in physical structure or function of the organ.

In some embodiments, the use of the method of the present invention can ameliorate organ transplantation by administering to the isolated (transplanted) organ an amount effective of an IL-33 antagonist. Accordingly, in some embodiments, the organ is destined to be transplanted in a recipient. The method is thus performed ex vivo in an isolated organ.

In some embodiments, the transplanted organ is a cadaverous organ, and in those instances in which the organ is obtained from a cadaverous donor, the IL-33 antagonist can be administered to either the cadaver or the extracted organ. In some embodiments, the transplanted organ is a living organ donation, and in those instances the IL-33 antagonist can be administered to the extracted organ.

In some embodiments, the organ is isolated and is perfused with the effective amount of the IL-33 antagonist.

In some embodiments, the transplanted organ is the subject of a warm ischemia and/or cold ischemia.

As used herein, the term "warm ischemia" has its general meaning in the art and is used to describe ischemia of cells and tissues under normothermic conditions.

As used herein, the term "cold ischemia" has its general meaning in the art and refers to the organ chilling during decreased blood perfusion or in the absence of blood supply. In some embodiments, the effective amount of the IL-33 antagonist is administered during the cold ischemia time. As used herein, the term "cold ischemia time" or "CIT" has its general meaning in the art and refers to the time which extends from the initiation of cold preservation of the recovered organ to restoration of warm circulation after transplantation. There is variability by accepting surgeon/center and by donor and recipient characteristics. Intuitively, shorter CIT is better. For kidney transplantation, the CIT should be inferior to 24 hours; for pancreas transplantation, the CIT should be inferior to 18 hours and for liver transplantation, the CIT should be inferior to 8 hours (Bernat J L, D'Alessandro A M, Port F K, Bleck T P, Heard S O, Medina J, et al. Report of a National Conference on Donation after cardiac death. Am J Transplant. 2006; 6:281-91).

In some embodiments, the use of the method of the present invention can ameliorate organ protection surgical procedure requiring stopping of blood supply to an organ followed by reperfusion. Examples of surgical procedures generating a risk of ischemia reperfusion injury include liver resection; revascularization following myocardial infarction, such as by thrombolytic therapy, stenting, or surgical repair; revascularization following stroke, such as by thrombolytic therapy or surgical repair; or revascularization following vascular injury including repair or reattachment of a limb following ischemic injury or surgical repair of an aneurysm. Other examples are surgery of the upper or lower gastrointestinal tract including laparoscopic procedures, open heart surgery with or without heart/lung machine, nose and throat surgery, vascular surgery, neurological (brain) surgery, transplantations (liver, heart, lung, kidney, intestinal), surgeries on the liver and cesarean sections. In some embodiments, the surgical procedure is a Coronary Artery Bypass Surgery, also known as coronary artery bypass graft (CABG) surgery or heart bypass or just bypass surgery which is a surgical procedure performed to relieve angina and reduce the risk of death from coronary artery disease. Arteries or veins from elsewhere in the patient's body are grafted to the coronary arteries to bypass atherosclerotic narrowings and improve the blood supply to the coronary circulation supplying the myocardium (heart muscle). This surgery is usually performed with the heart stopped, necessitating the usage of cardiopulmonary bypass; techniques are available to perform CABG on a beating heart, so-called "off-pump" surgery. In some embodiments, the method of the present invention can be used in any surgical procedure requiring clamping of blood supply to an organ. In particular, the present method of the invention is applied to all surgical procedures, which involve the connection of two blood vessels, e.g., coronary bypass, peripheral bypass, hemodialysis access (creation of a fistula), and free-flap surgery (breast and face reconstruction surgery). More particularly, the method of the present invention may be applied to any surgical procedure that requires anastomosis. The term "anastomosis" as used herein refers to a surgical connection between tubular structures, such as blood vessels. Typically, the effective amount of the IL-33 antagonist may be administered to the patient before, during or after the surgical procedure. In particular, the effective amount of the IL-33 antagonist is administered to the patient during the reperfusion of the organ.

The method of the present invention may be applied to any ischemic insult or event. Tissues that are particularly susceptible to ischemic events include myocardial, vascular and neuronal tissue (particularly cerebral tissue). Other tissues that are susceptible to ischemia include tissue from the gut, liver, kidney and eye. The need for cardioprotection may arise due to certain physiological disorders such as unstable angina, during trauma or periods of cardiac arrest. In addition, disorders such as stroke, transient ischemic attacks or impending stroke (amarosis fugax) are candidate conditions for treatment using the method of the invention. Where stroke giving rise to a risk of secondary stroke occurs, or another condition giving rise to a risk of stroke within hours or days occurs, the method can be applied to diminish such risk. Those of skill in the art will recognize circumstances associated with increased risk of other ischemic tissue injury. Such disease states include mesenteric artery insufficiency, renal artery stenosis, hepatic vein thrombosis, peripheral vascular insufficiency, multiple trauma, sepsis and multi-organ system failure. Other ischemic events include angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia such as a cerebrovascular accident CVA). Ischemia/reperfusion may damage tissues other than those of the myocardium. The method provided could be useful in reducing ischemia reperfusion injury in the tissue of the brain, liver, gut, kidney, bowel, or in any other tissue. Additional applications include blunt or penetrating trauma that results in interruption of blood flow to the viceral organs including those arising from penetrating wounds to the abdomen resulting from gun shot wounds, stab wounds or from penetrating wounds or blunt abdominal trauma secondary to deacceleration injury and/or motor vehicle accidents. Other preferred applications include diseases or procedures that result in systemic hypotension that either disrupts or decreases the flow of blood to the visceral organs, including hemorrhagic shock due to blood loss, cardiogenic shock due to myocardial infarction or cardiac failure, neurogenic shock or anaphylaxis.

In some embodiments, the method of the present invention is particularly suitable for preventing progression to chronic kidney disease (CKD) after an acute kidney injury (AKI). As used herein, the term "chronic kidney disease" (CKD) refers to a progressive loss in renal function over a period of months or years. CKD has its general meaning in the art and is used to classify numerous conditions that affect the kidney, destruction of the renal parenchyma and the loss of functional nephrons or glomeruli. It should be further noted that CKD can result from different causes, but the final pathway remains renal fibrosis. The term "acute kidney injury" or "acute kidney failure" is typically identified by a rapid deterioration in renal function sufficient to result in the accumulation of nitrogenous wastes in the body (see, e.g., Anderson and Schrier (1994), in Harrison's Principles of Internal Medicine, 13th edition, Isselbacher et al, eds., McGraw Hill Text, New York). Rates of increase in BUN of at least 4 to 8 mmol/L/day (10 to 20 mg/dL/day), and rates of increase of serum creatinine of at least 40 to 80 μmηI/L/day (0.5 to 1.0 mg/dL/day), are typical in acute renal failure. Urinary samples also may contain tubular injury residue in patients suffering from acute kidney injury. In subjects which are catabolic (or hypercatabolic), rates of increase in BUN may exceed 100/mg/dL/day. Rates of increase in BUN or serum creatinine may be determined by serial blood tests and, preferably, at least two blood tests are conducted over a period of between 6 and 72 hours or, more preferably, 12 and 24 hours. A distinction is sometimes made between "acute" renal failure (deterioration over a period of days) and "rapidly progressive" renal failure (deterioration over a period of weeks). As used herein, however, the phrase "acute kidney injury" is intended to embrace both syndromes. Acute kidney injury is regularly identified by clinicians, as discussed above. AKI may result from abnormalities of the vasculature such as vasoconstrictive disease (e.g., malignant hypertension, scleroderma, hemolytic uremic syndrome, thrombotic thrombocytopenic purpura) and vasculitis (e.g., polyarteritis nodosa, hypersensitivity angiitis, serum sickness, Wegener's granulomatosis, giant cell arteritis, mixed cryoglobulinemia, Henoch-Schonlein purpura, systemic lupus erythematosus). AKI may also result from abnormalities of the glomeruli such as post-infectious abnormalities (e.g., post-streptococcal, pneumococcal, gonococcal, staphylococcal, enterococcal, viral [e.g., hepatitis B and C, mumps, measles, Epstein-Barr], malarial, or related to brucellosis, Legionella, Listeria, shunt nephritis, leprosy, leptospirosis, or visceral abscesses) and non-infectious abnormalities (e.g., rapidly progressive glomerulonephritis, membranoproliferative glomerulonephritis, Goodpasture's syndrome, systemic lupus erythematosus, Wegener's granulomatosis). In some embodiments, AKI may result from acute interstitial nephritis resulting from drug related causes (e.g., penicillins, sulfonamides, carbenicillin, cephalosporin, erythromycin, nafcillin, oxacillin, nonsteroidal antiinflammatory agents, diuretics (furosemide, ethacrynic acid, thiazide, spironolactone, mercurials), phenytoin, phenobarbital, probenicid, allopurinol, cimetidine), infection related causes (e.g., acute pyelonephritis, streptococcal, staphylococcal, leptospirosis, malaria, salmonellosis), papillary necrosis (e.g., associated with diabetes mellitus, sickle cell diseases, analgesic abuse, alcoholism), and other, miscellaneous causes (e.g., sarcoidosis, leukemia, lymphoma). Sime embodiments, AKI may result from intratubular obstruction from crystal deposition (e.g., uric acid, oxalate, methotrexate) or multiple myeloma and light chain disease. In some embodiments, AKI may result from Acute tubular necrosis resulting from nephrotoxins (e.g., antimicrobials such as aminoglycosides, tetracyclines, amphotericin, polymyxin, cephalosporins), heavy metals (e.g., mercury, lead, arsenic, gold salts, barium), and other, miscellaneous chemical agents (e.g., cisplatin, doxorubicin, streptozocin, methoxyflurane, halothane, ethylene glycol, carbon tetrachloride), or from ischemia (e.g., hemorrhage, hypotension, sepsis, burns, renal infarction, renal artery dissection, rhabdomyolysis trauma), or other miscellaneous causes (e.g., contrast agents, transfusion reactions, myoglobinemia, heat stroke, snake and spider bites). As used herein, the term "IL-33" has its general meaning in the art and refers to the human IL-33 protein having the amino acid sequence as set forth in NCBI accession Nos. NP_254274.1 (human isoform 1), NP_001186569.1 (human isoform 2), or NP_001186570.1 (human isoform 3). All references to proteins, polypeptides and protein fragments herein are intended to refer to the human version of the respective protein, polypeptide or protein fragment unless explicitly specified as being from a non-human species (e.g., "mouse IL-33," "monkey IL-33," etc.).

As used herein the term "ST2" has its general meaning in the art and refers to the receptor of IL-33 having the amino acid sequence as set forth in NCBI Accession No. NP_057316.3.

As used herein, the term "IL-33 antagonist" refers to a compound that inhibits the activity or expression of IL-33. In particular, an IL-33 antagonist refers to any compound that is capable of binding IL-33 or its receptor (ST2) and blocking, attenuating or otherwise interfering with IL-33 signalling and/or the interaction between IL-33 and a cell surface receptor (i.e. ST2). Typically, an IL-33 antagonist is a small organic molecule, a polypeptide, an aptamer, an antibody, an intra-antibody, an oligonucleotide or a ribozyme.

In some embodiments, the IL-33 antagonist is an antibody having binding affinity for IL-33. In some embodiments, the IL-33 antagonist is an antibody directed against the extracellular domain of ST2. In some embodiments, the antibody of the present invention is capable of inhibiting the binding of IL-33 to ST2. In some embodiments, the IL-33 antagonist is an antibody having binding affinity for the region of IL-33 which binds to ST2. In some embodiments, the IL-33 antagonist is an antibody having binding affinity for the domain of ST2 which binds to IL-33.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545, 807, 6,150,584, and references cited therein, the contents of which are incorporated herein by reference.

In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody are also "nanobody®".

In some embodiments, the antibody comprises human heavy chain constant regions sequences but will not induce antibody dependent cellular cytotoxicity (ADCC). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab')2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. Nos. 6,194,551 by ldusogie et al.

In some embodiments, the IL-33 antagonist is a polypeptide comprising a functional equivalent of ST2. As used herein, a "functional equivalent of ST2" is a polypeptide which is capable of binding to IL-33, thereby preventing its interaction with ST2. The term "functional equivalent" includes fragments, mutants, and muteins of ST2. The term "functionally equivalent" thus includes any equivalent of ST2 obtained by altering the amino acid sequence, for example by one or more amino acid deletions, substitutions or additions such that the protein analogue retains the ability to bind to a ST2. Amino acid substitutions may be made, for example, by point mutation of the DNA encoding the amino acid sequence. Functional equivalents include molecules that bind IL-33 and comprise all or a portion of the extracellular domains of ST2 so as to form a soluble receptor that is capable to trap IL-33. Thus the functional equivalents include soluble forms of the ST2. A suitable soluble form of these proteins, or functional equivalents thereof, might comprise, for example, a truncated form of the protein from which the transmembrane domain has been removed by chemical, proteolytic or recombinant methods. Typically, the functional equivalent is at least 80% homologous to the corresponding protein. In some embodiments, the functional equivalent is at least 90% homologous as assessed by any conventional analysis algorithm. The term "a functionally equivalent fragment" as used herein also may mean any fragment or assembly of fragments of ST2 that binds to IL-33. Accordingly the present invention provides a polypeptide capable of inhibiting binding of ST2 to IL-33, which polypeptide comprises consecutive amino acids having a sequence which corresponds to the sequence of at least a portion of an extracellular domain of ST2, which portion binds to IL-33. In some embodiments, the polypeptide comprises an extracellular domain of ST2.

In some embodiments, the polypeptide comprises a functional equivalent of ST2 which is fused to an immunoglobulin constant domain (Fc region) to form an immunoadhesin. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. The immunoglobulin sequence typically, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but typically IgG1 or IgG3. In some embodiments, the functional equivalent of the PD-1 or IL-33 and the immunoglobulin sequence portion of the immunoadhesin are linked by a minimal linker. As used herein, the term "linker" refers to a sequence of at least one amino acid that links the polypeptide of the invention and the immunoglobulin sequence portion. Such a linker may be useful to prevent steric hindrances. In some embodiments, the linker has 4; 5; 6; 7; 8; 9; 10; 11; 12; 13; 14; 15; 16; 17; 18; 19; 20; 21; 22; 23; 24; 25; 26; 27; 28; 29; 30 amino acid residues. One useful group of linker sequences are linkers derived from the hinge region of heavy chain antibodies as described in WO 96/34103 and WO 94/04678. Other examples are poly-alanine linker sequences. In some embodiments, the IL-33 antagonist is an inhibitor of IL-33 or ST2 expression respectively. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, antisense oligonucleotides, including anti-sense RNA molecules and anti-sense DNA molecules, would act to directly block the translation of IL-33 or ST2 mRNA by binding thereto and thus preventing protein translation or increasing mRNA degradation, thus decreasing the level of IL-33 or ST2, and thus activity, in a cell. For example, antisense oligonucleotides of at least about 15 bases and complementary to unique regions of the mRNA transcript sequence encoding IL-33 or ST2 can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. IL-33 or ST2 gene expression can be reduced by contacting a patient or cell with a small double stranded RNA (dsRNA), or a vector or construct causing the production of a small double stranded RNA, such that IL-33 or ST2 gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing IL-33 or ST2. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. In some embodiments, the inhibitor of expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, and cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR). In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences. In some embodiment, the endonuclease is CRISPR-cas9 which is from Streptococcus pyogenes. The CRISPR/Cas9 system has been described in U.S. Pat. No. 8,697,359 B1 and US 2014/0068797. In some embodiment, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

As used herein, the term "effective amount" refers to an amount effective of the IL-33 antagonist, at dosages and for periods of time necessary, to achieve a desired therapeutic result (i.e. preventing ischemia reperfusion injury). A therapeutically effective amount of the IL-33 antagonist may vary according to factors such as the disease state, age, sex, and weight of the individual, and the ability of the IL-33 antagonist to elicit a desired response in the individual. A therapeutically effective amount is also one in which any toxic or detrimental effects of the antibody or antibody portion are outweighed by the therapeutically beneficial effects. The efficient dosages and dosage regimens for the IL-33 antagonist depend on the disease or condition to be treated and may be determined by the persons skilled in the art. A physician having ordinary skill in the art may readily determine and prescribe the effective amount of the pharmaceutical composition required. For example, the physician could start doses of IL-33 antagonist employed in the pharmaceutical composition at levels lower than that required achieving the desired therapeutic effect and gradually increasing the dosage until the desired effect is achieved. In general, a suitable dose of a composition of the present invention will be that amount of the compound, which is the lowest dose effective to produce a therapeutic effect according to a particular dosage regimen. Such an effective dose will generally depend upon the factors described above.

Typically, the IL-33 antagonist of the present invention is administered directly into the subject or isolated organ using injection, pump device and/or any machine (e.g. bypass machine).

Typically, the IL-33 antagonist is administered to the patient in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene- block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the IL-33 antagonist is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. In some embodiments, an isolated organ suitable for transplantation is perfused with a preservation solution which comprises the effective amount of the IL-33 antagonist. As used herein, the terms "preservation solution" or "organ preservation solution" refer to an aqueous solution having a pH between 6.5 and 7.5, including salts, preferably chloride, sulfate, sodium, calcium, magnesium and potassium; sugars, preferably mannitol, raffinose, sucrose, glucose, fructose, lactobionate (which is a water resistant), or gluconate; antioxidants, for instance glutathione; active agents, for instance xanthine oxidase inhibitors such as allopurinol, lactates, amino acids such as histidine, glutamic acid (or glutamate), tryptophan; and optionally colloids such as hydroxyethyl starch, polyethylene glycol or dextran. In some embodiments of the invention, the organ preservation solution is selected from:

the solution from the University of Wisconsin (UW or ViaSpan®), which has an osmolality of 320 mOsmol/kg and a pH of 7.4, of the following formulation for one liter in water: potassium lactobionate: 100 mM, KOH: 100 mM, NaOH: 27 mM, KH2PO4: 25 mM, MgSO4: 5 mM, Raffinose: 30 mM, Adenosine: 5 mM, Glutathione: 3 mM, Allopurinol: 1 mM, Hydroxyethyl starch: 50 g/L, IGL-1®, having an osmolality of 320 mOsm/kg and a pH of 7.4, of the following formulation, per liter in water: NaCL: 125 mM, KH2PO4: 25 mM, MgSO4: 5 mM, Raffinose: 30 mM, potassium lactobionate: 100 mM, Glutathione: 3 mM, Allopurinol: 1 mM, Adenosine: 5 mM, Polyethylene glycol (molecular weight: 35 kDa): 1 g/L, Celsior®, having an osmolality of 320 mOsm/kg and a pH of 7.3, of the following formulation per liter in water:

Glutathione: 3 mM, Mannitol: 60 mM, lactobionic acid: 80 mM, Glutamic acid: 20 mM, NaOH: 100 mM, calcium chloride dehydrate: 0.25 mM, MgSO4: 1.2 mM, KCl: 15 mM, magnesium chloride hexahydrate: 13 mM, Histidine 30 mM, BMPS Belzer® or Belzer solution infusion machine or KPS1, especially comprising 100 mEq/L of sodium, 25 mEq/L potassium, pH 7.4 at ambient temperature, and having an osmolarity of 300 mOsm/L, Custodiol® HTK solution having the following formulation per liter in water, the pH of 15 being 7.20 at room temperature, and the osmolality was 310 mOsm/kg: NaCl: 18.0 mM, KCl: 15.0 mM, KH2PO4: 9 mM, 2-ketoglutarate hydrogenated potassium: 1.0 mM, hexahydrate magnesium chloride: 4.0 mM; histidine, HCl, H2O: 18.0 mM, histidine: 198.0 mM, Tryptophan: 2.0 mM, Mannitol: 30.0 mM, calcium chloride dihydrate: 0.015 mM Soltran®, having an osmolality of 486 mOsm/kg and a pH of 7.1 and the following formulation per liter in water: Sodium: 84 mM, Potassium: 80 mM, Magnesium: 41 mM, Sulfate: 41 mM, Mannitol 33.8 g/l, Citrate: 54 mM, Glucose: 194 mM, Perfadex®, having an osmolarity of 295 mOsmol/L and the following formulation in water: 50 g/L of Dextran 40 (molecular weight: 40,000), Na+138 mM, K+6 mM, Mg2+: 0.8 mM, Cl−142 mM, SO42 0.8 mM, (+H2PO4—HP)42-): 0.8 mM, glucose 5 mM, Ringer lactate®, of the following formulation, in water, the pH being between 6.0 and 7.5 at ambient temperature, and having an osmolarity of 276.8 mOsmol/L: Na+130 mM, K+5.4 mM, Ca2+: 1.8 mM, Cl—: 111 mM, Lactate: 27.7 mM, Plegisol®, of the following formulation, in water: KCI: 1.193 g/l, MgCl2, H2O: 3.253 g/L, NaCl: 6.43 g/L, CaCl2: 0.176 g/l, Solution Hospital Edouard Henriot, of the following formulation in water, the pH being equal to 7.4 at ambient temperature, and having an osmolarity of 320 mOsmol/L: KOH: 25 mM, NaOH: 125 mm, KH2PO4: 25 mM, MgCl2: 5 mM, MgSO4: 5 mM, Raffinose: 30 mM, lactobionate: 100 mM, Glutathione: 3 mM, Allopurinol: 1 mM, Adenosine: 5 mM, Hydroxyethyl starch 50 g/L, And Steen® solution comprising human serum albumin, dextran and extracellular electrolyte with a low concentration of potassium.

All these organ preservation solutions are commercial products. Typically, a device for preserving an organ is used wherein said device comprises an organ container filled with a preservation solution, characterized in that said device further comprises one or more mean for injecting one or more compound (e.g. the IL-33 antagonist) into the organ container.

A further object of the present invention relates to a device for preserving an organ, said device comprising an organ container filled with a preservation solution, characterized in that said device further comprises one or more mean for injecting an IL-33 antagonist into the organ container. In some embodiments, the device according to the invention comprises an alarm which gives the health professional notice of the administration moment of the IL-33 antagonist by the injected mean. In some embodiments, the device according to the invention is programmable in order to administer automatically the IL-33 antagonist by the injected mean when needed/programmed. In some embodiments, the device according to the invention comprises an organ container, a computing system and means for injected the IL-33 antagonist of the present invention. The organ container is a sterile receptacle for the organ. The organ container is filled with a preservation solution. The computing system, or similar electronic computing device, is adapted to manipulate and/or transform data represented as physical, such as electronic, quantities within the computing system's registers and/or memories into other data similarly represented as physical quantities within the computing system's memories, registers or other such information storage, transmission or display devices. The computing system comprises a display unit for data presentation and data entry. The mean for injecting the IL-33 antagonist comprises a container containing the antagonist and a device permitting the injection of the compound into the organ chamber. For example, the mean is a syringe. In some embodiments, the device comprises a software. The software permits the implementation of the method according to the invention and plays a role of coordination of the injection times of the IL-33 antagonist to be injected. In some embodiments, the organ container is hermetically sealed against fluid and pressure. In some embodiments, the device according to the invention further comprises: one or several circulatory system, one or several refrigeration mean, one or several oxygenator, one or several pump, one or several filter, one or several probe or sensor detecting, for instance, temperature, pressure or any compound concentration, and/or one or several software.

The invention will be further illustrated by the following figures and examples. However, these examples and figures should not be interpreted in any way as limiting the scope of the present invention.

FIGURES

FIG. 1: IL-33-deficient mice are protected against IRI. Wild-type (WT) and IL-33$^{Gt/Gt}$ (IL-33-deficient) mice were subjected to sham surgery (Sham) or 32 minutes of unilateral ischemia (IRI) following contralateral nephrectomy (Ctr). After 24 hours (T24) of reperfusion, kidneys and peripheral blood were obtained (5-8 animals per group). (A-C) Acute kidney injury changes are attenuated in IL-33-deficient mice. IL-33-deficient mice exhibited decreased blood creatinine (A) and urea nitrogen (BUN) (B) levels. (C) tubular injury scores (5-8 mice per group). Two-tailed Mann-Whitney U test was used for two group comparisons, and one-way ANOVA followed by Tukey post-test for three or more group comparisons. *P<0.05; P<0.01; *P<0.001. (D) IRI-induced oxidative stress generation is attenuated in IL-33-deficient mice. ROS production in renal tissue from WT and IL-33-deficient mice was measured using the fluorogenic probe called CellROX® green. Quantification of CellROX ® fluorescence intensity (3 animals per group). AU: arbitrary unit. Two-tailed Mann-Whitney U test was used for two group comparisons, and one-way ANOVA followed by Tukey post-test for three or more group comparisons. *P<0.05; **P<0.01. Note that we found no difference between sham and Ctr values (data not shown), indicating the absence of a significant Sham effect for all the tested parameters.

Figure 2:
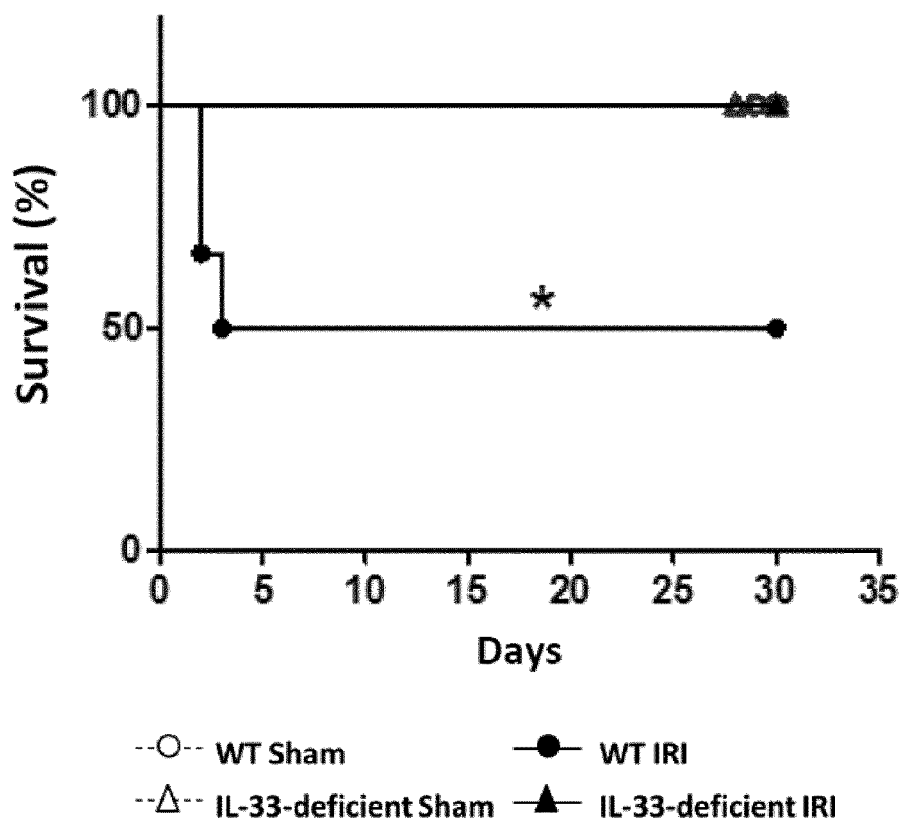

FIG. 2: Mortality is reduced in IL-33-deficient mice. Wild-type (WT) and IL-33$^{Gt/Gt}$ (IL-33-deficient) mice were subjected to sham surgery (Sham; 3 animals per group) or 32 minutes of unilateral ischemia (IRI; 6 animals per group) after contralateral nephrectomy. Kaplan-Meier survival curves for sham-operated and IRI WT and IL-33-deficient mice. Thirty days after IRI induction, a survival rate of 100% was observed in IL-33-deficient mice whereas 50% of WT mice succumbed within the first 3-4 days. Survival distribution of the WT IR group was significantly different from all other groups of mice. (Mantel-Cox, *P<0.05). IRI is presumably the cause of mortality because the vast majority of ischemia-reperfusion-induced WT mice were still anuric at 2-3 days post-IRI.

Figure 3A:
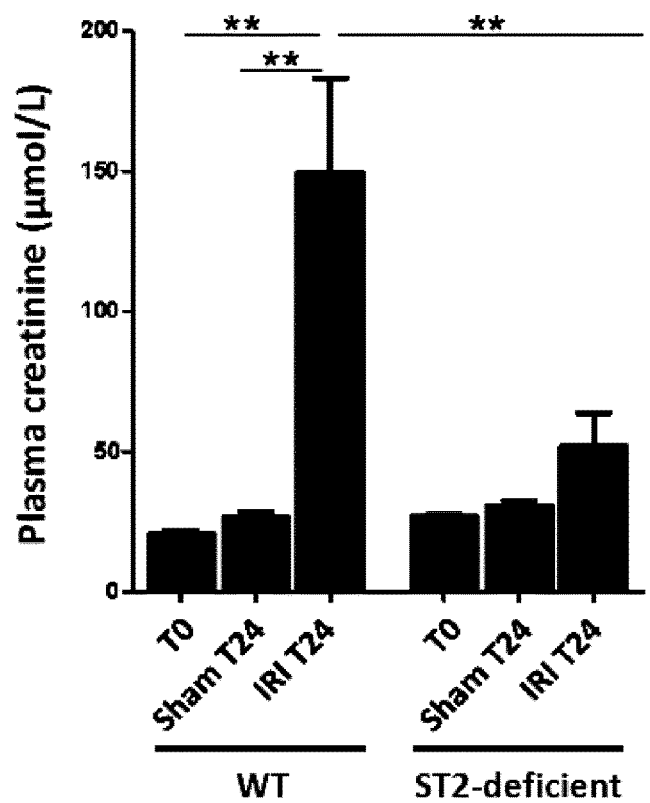
Figure 3B:
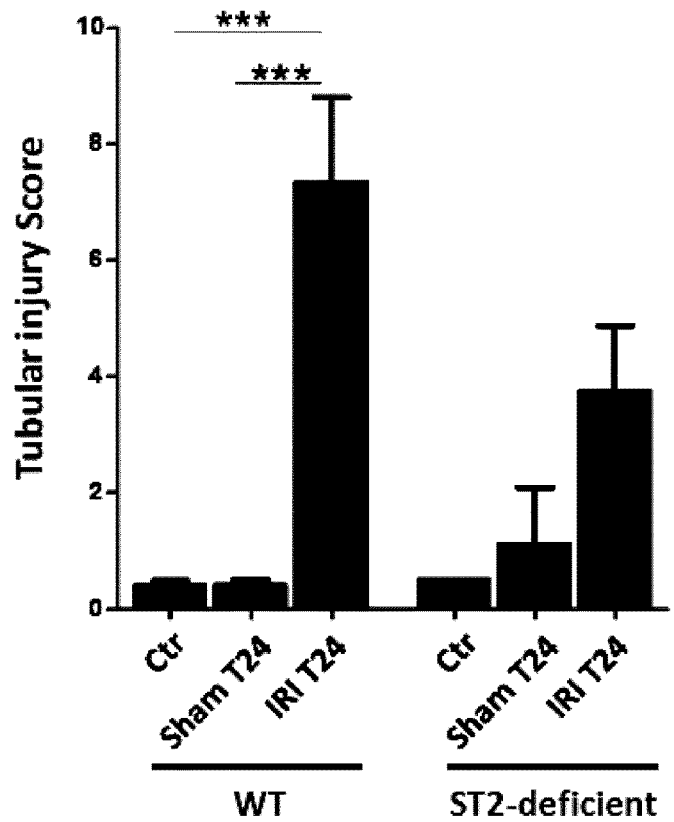

FIG. 3: ST2-deficient mice are protected against IRI. Wild-type (WT) and ST2KO (ST2-deficient) mice were subjected to sham surgery (Sham) or 32 minutes of unilateral ischemia (IRI) following contralateral nephrectomy (Ctr). After 24 hours (T24) of reperfusion, kidneys were obtained (4-6 animals per group). At T24 post-IRI, ST2-deficient mice demonstrated less elevated blood creatinine levels (A) and attenuated tubulointerstitial damage (B) as compared to their WT counterparts. Control plasma (T0) was obtained from naïve animals. Tubular injury was assessed with periodic acid-Shiff (PAS) staining. Sham and healthy Ctr kidneys from both WT and ST2-deficient mice exhibited normal tubular structure. Data are expressed as means±SEM. One-way ANOVA followed by Tukey post-test was used for three or more group comparisons. P<0.01; *P<0.001.

Figure 4:
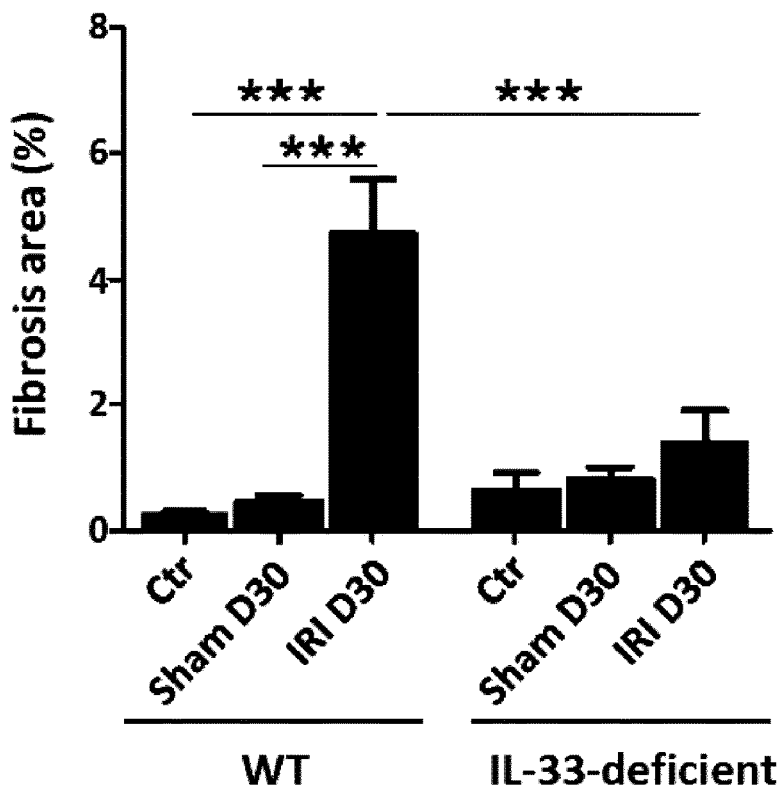

FIG. 4: Collagen deposition after IRI is reduced in IL-33-deficient mice. Wildtype (WT) and IL-33$^{Gt/Gt}$ (IL-33-deficient) mice were subjected to sham surgery (Sham; n=3) or 32 minutes of unilateral ischemia (IRI; n=6) after contralateral nephrectomy (Ctr). At day 30 (D30) post-reperfusion, kidneys were obtained from surviving mice. Fibrosis was measured using Sirius red staining. Significant collagen deposition in kidneys was found at D30 post-IRI in kidneys from WT (n=3) but not in IL-33-deficient (n=6) mice, as compared to their healthy Ctr (n=3) or Sham (n=3) counterparts. We attributed the lesser progression to fibrosis in IL-33-deficient mice to less initial AKI rather than to loss of IL-33. Data are expressed as means±SEM. Two-tailed Mann-Whitney U test was used for two group comparisons, and one-way ANOVA followed by Tukey post-test for three or more group comparisons. *P<0.05; P<0.01; *P<0.001.

EXAMPLE

Material & Methods

Animals

Wild-type C57BL/6 mice were purchased from Janvier Labs (Le Genest-Saint-Isle, France). IL-33-deficient C57BL/6 mice with a Lac-z gene-trap (Gt) reporter (IL-33$^{Gt/Gt}$) were generated as described by Pichery et al.[52]. Jα18KO C57BL/6 mice (lacking iNKT cells) and ST2KO C57BL/6 mice were kindly provided by M Taniguchi[53] and A McKenzie[54], respectively. All mice were maintained in our animal facilities under specific pathogen-free conditions. Ten-to-twelve-week-old male mice weighing between 25 and 30 g were used in all experiments. Animal care and manipulations for experimentation were conducted in accordance with the guidelines of the French Agriculture and Forestry Ministry (decree 87849) and of European Communities Council Directive (86/609/EEC) and were approved by the local ethics committee (COMETHEA: CE2012-06).

Mouse Model of Ischemic-Reperfusion Kidney Injury

An established mouse model of unilateral renal ischemia-reperfusion was used. Briefly, mice were anesthetized with isoflurane (2% for induction and 1.5% for maintenance). After flank incision, the right renal pedicle was clamped using a straight Schwartz Micro clip (Fine Science Tools, Heidelberg, Germany) for 32 minutes, and then released. This duration of ischemia was chosen to induce kidney injury of notable severity without a high mortality rate, permitting evaluation of the fibrosis process after functional recovery. The left contralateral kidney (Ctr) was ligated and removed before IRI induction and was used as healthy and internal control for comparison with the IRI and sham kidneys. Sham-operated mice underwent identical surgical procedures without clamping of the renal pedicle, and served as controls for IRI mice. Body temperature was controlled throughout the procedure. Animals were then allowed to recover, with free access to food and water. Blood was collected from retro-orbital sinus of isoflurane-anesthetized mice, and right kidneys were removed 1, 3, 6, or 24 hours of reperfusion.

Renal Function

Plasma creatinine and blood urea nitrogen (BUN) were measured 1, 3, 6, or 24 hours post-reperfusion to assess renal function, using high-performance liquid chromatography as reported[55] and the Cobas C701 automatic analyzer (Roche Diagnostic), respectively.

Cytokine and Chemokine Measurement

Mouse IL-33 and MCP-1 (Quantikine kit) and mouse IL-17A and human IL-8 (Duotest) were quantified in plasma by sandwich ELISA (R&D Systems) according to the manufacturer's instructions. Mouse IFN-γ was quantified by standard sandwich ELISA, as previously described[29]. Luminex technology was used according to the manufacturer's instructions to measure mouse IL-12p70, MIP-2, CCL5/RANTES, CXCL9/MIG and CXCL10 in plasma (R&D Systems).

Renal Histopathology

Kidneys were fixed in 4% formol, embedded in paraffin wax and sectioned at 3.5 μm. Periodic-acid-Schiff (PAS) staining was used to assess tubular injury. Histological changes were evaluated by assessment of tubules that displayed: dilatation, cell necrosis and cast formation, loss of brush border in addition to interstitial edema and interstitial inflammation. All histologic examinations were performed by a renal pathologist (JMG) in a blinded fashion using a semi-quantitative scale as follows: 0 (no damage); 1 (damage affecting less than 25% of the whole kidney sections), 2 (damage affecting 25-50% of kidney sections), 3 (damage affecting 50% or more of the whole kidney section).

Immunostaining and Immunoblotting

A polyclonal goat anti-mouse IL-33 antibody (R&D Systems, clone AF3626) that recognizes mouse full-length (34-37 kD) and cleaved IL-33 (19-22 kD) was used for immunostaining and western blot analysis.

For immunofluorescence studies, 5 μm cryosections were fixed 1 hour at 4° C. in 4% paraformaldehyde (PFA). Sections were blocked and permeabilized with 3% BSA, 0.3% Triton-X100, and then stained with primary antibody overnight at 4° C. as follows: goat anti-mouse IL-33 (1:500), rat anti-mouse CD31 (1:500, BD Biosciences, clone MEC13.3), and APC-conjugated anti CD45 (1:200, BD Biosciences, clone 30-F11). Slides were incubated for 1 hour at room temperature with secondary antibodies as follows: Alexa Fluor 488 donkey anti-rat IgG (1:250; Life Technologies, A21208), Alexa Fluor 568 donkey anti-goat IgG (1:500; Life Technologies, A11057) were used as secondary antibodies. Nuclear staining was performed with DAPI (4,6-Diamidino-2-phenylindole) (SouthernBiotech).

For IL-33 detection by immunohistochemistry, 5 µm cryosections were fixed in acetone and immersed in peroxidase block solution (Dako) to eliminate endogenous peroxidase activity. The sections were incubated with 1% FBS and then with goat anti-mouse IL-33 antibody (1:200) for 4 hours at room temperature. After incubation with the HRP-conjugated rabbit anti-goat IgG secondary antibody (1:200, Invitrogen), the immune complexes were visualized using DAB substrate (Dako). Images were obtained by fluorescence (Olympus BX41) or confocal (Olympus FV1000) microscopy using the same laser power and gain intensity for all pictures. IL-33 expression was digitally quantified using Visilog 7.1® software. For each animal, 5 fields were analyzed.

For immunoblotting, kidney homogenates were lysed in RIPA lysis buffer (20 mM Tris-HCl (pH 7.5), 150 mM NaCl, 1 mM $Na_2EDTA$, 1 mM EGTA, 1% Nonidet P-40, 1% sodium deoxycholate, supplemented with phosphatase and protease inhibitor cocktail (Santa Cruz). The supernatants were collected after centrifugation at 14 000 g for 10 min at 4° C. Kidney lysates were resolved on SDS-PAGE and nitrocellulose membranes were blocked with non-fat dry milk and incubated overnight at 4° C. with goat anti-mouse IL-33 antibody (1:500), and then with an HRP-conjugated rabbit anti-goat polyclonal antibody (1:2000, Invitrogen). The immunoreactive proteins were visualized with ECL Prime Western blotting detection reagent (Amersham), using the ChemiDoc™ MP imaging system (Bio-Rad). Relative protein levels were normalized to GAPDH as a loading control (1:2000, Cell signaling).

Quantitative Evaluation of Fibrosis

Cryoconserved kidney sections (5 µm) were fixed for 10 minutes in cold acetone and then stained with Sirius red (Diapath) for 30 minutes at room temperature. Sections were washed in acidified water, ethanol (95%, then 100%), and mounted for light macroscopy analysis. The amount of collagen deposition (red area), normalized over the surface area analyzed, was digitally quantified using Visilog 7.1® software.

RNA extraction and Real-Time quantitative Reverse Transcription (RTqPCR)

Total RNA was extracted from mouse renal tissue using the Nucleospin RNA extraction kit, according to the manufacturer's instructions (Macherey-Nagel). Total RNA (1 µg) from each sample was retro-transcribed into cDNA using the qScript cDNA Supermix (Quanta Biosciences). Quantitative real-time polymerase chain reaction (PCR) was performed on the Rotor-Gene Q Lightcycler (Qiagen) using the 2× Perfecta SYBER Green Mix (Quanta Biosciences) and 500 nM of the specific primer for mouse 11-33. Results were then normalized with Nono mRNA content.

Kidney Leucocyte Isolation and Flow Cytometry Analysis

Fresh kidneys were minced and passed through a 70-µm strainer (BD Falcon), and centrifuged at 300 g for 10 minutes in complete RPMI 1640 (Life Technologies). The cell pellet was resuspended in 36% Percoll solution (GE Healthcare) and then loaded on a layer of 72% Percoll solution followed by centrifugation at 500 g for 20 minutes at room temperature. Leucocytes were harvested from the interface layer of Percoll and washed in PBS1X. Phenotypic analysis of renal leucocytes was performed by flow cytometry using the following mAbs: CD45-BV510 (Clone 30-F11; Biolegend), CD11b-PE (Clone: M1/70; Biolegend), F4/80-FITC (Clone: BM8; Biolegend), GR-1-BV421 (Clone: RB6-8C5; Biolegend), NK1.1-APC (Clone: PK136; Biolegend), NK1.1-PerCpCy5.5 (Clone: PK136; BD Biosciences), CD3-PerCpCy5.5 (Clone: 17A2; Biolegend) and ST2-APC (Clone: 245707; R&D systems). To identify iNKT cells, samples were stained with the a-galactosylceramide analog PBS57 loaded with mouse CD1d tetramer (TT) conjugated to BV421 or its unloaded tetramer used as a control.

For intracellular cytokine staining, cells were isolated and incubated 4-6 hours in the presence of Brefeldin A (Golgistop, BD Biosciences). After staining with surface marker antibodies, cells were permeabilized with the Fix/Perm buffer (BD Biosciences) and incubated with anti-mouse IFN-γ-PE-Cy7 (Clone: XMG102; BD Biosciences) and anti-mouse IL-17A-PE (Clone: TC11-18H10; BD Biosciences) antibodies. Cells were analyzed using BD FACS Verse™ cytometer (BD Biosciences) and FlowJo v7 software (TreeStar, Inc). Dead cells were excluded using the Live/Dead Fixable Near-IR Dead Cell Stain kit (Life technologies).

iNKT Cell Purification and Culture iNKT (PBS57-loaded TT(+) CD5(+)) cells were sorted by FACS as previously described[29]. Prior to sorting, freshly isolated splenocytes were enriched for iNKT cells by magnetic depletion of CD8, CD11b, CD62L and CD19 cells (Invitrogen Life Technology), according to the manufacturer's instructions. Sorted cells were routinely 97% pure. A total of $2.5 \times 10^4$ sorted iNKT were cultured for 48 hours in 200 µg/mL complete RPMI with or without coated anti-CD3 mAb (1 µg/mL, BD Pharmingen), in the presence or absence of murine IL-33 (10 ng/mL, R&D Systems) and/or murine IL-12 (20 ng/mL, R&D Systems) in round bottomed 96-well plates at 37° C. and 5% CO2. IFN-γ and IL-17A were measured in supernatants by ELISA.

Renal Proximal Tubule Epithelial Cell Cultures

Immortalized mouse kidney proximal tubule epithelial (TKPTS) cells were kindly provided by Professor Elsa Bello-Reuss (Texas) and sent by Dr Rafia Al-Lamki (from Dr Bradley's laboratory, Cambridge, UK). The human renal proximal tubule epithelial cell lines HRPTEC and HK-2 derived from normal kidney were purchased from ATCC and provided by Pr. Tauc (Sofia-Antipolis University, Nice, France), respectively. Cells were cultured in phenol red-free Dulbecco's modified Eagle's medium DMEM/F12 supplemented with 4% (HRPTEC), 5% (TKPTS) or 10% (HK-2) of FBS in a humidified atmosphere of 5% $CO_2$ at 37° C. The culture medium was refreshed every 2 days until cell confluence reached 70-80% and cells were further incubated for 24 or 48 hours in the presence or absence of the appropriate murine or human recombinant IL-33 (R&D Systems, 10-20 ng/mL). IL-8 and MCP-1 were measured in supernatants by ELISA.

Oxidative Stress Measurement

CellROX® Green Reagent (ThermoFisher Scientific) was used to evaluate kidney superoxide production reflecting oxidative stress. Kidney cryoconserved sections (5 µm) were incubated at 37° C. for 30 minutes in the dark with 5 µM of CellROX® Green Reagent. Samples were then washed with PBS1X, mounted with media containing DAPI (SouthernBiotech), and observed using the Olympus BX41 fluorescence microscope system. Oxidative stress was determined and calculated using Image J. Data were expressed in arbitrary units (AU) as percentage of Σ mean of positive-stained cells (green signal)/Σ mean of nucleus (blue signal). For each animal, 5-7fields were analyzed.

Statistical Analyses

Statistical analyses were performed using GraphPad Prism software, version 5.0. All the experimental groups were compared using the non-parametric Mann-Whitney U test to calculate P values of two groups, and one-way ANOVA for three or more groups followed by Tukey post-test. For survival analysis, the Kaplan-Meier plot with a log-rank test was used. P<0.05 was considered to be statistically significant. Data are shown as mean values±SEM.

Results

IL-33 is constitutively expressed in microvascular endothelial cell nuclei.

We first examined the expression of IL-33 and its localization in healthy kidneys from wild-type (WT) mice. IL-33 was clearly detected in periglomerular and peritubular areas by immunohistochemistry (data not shown), in accordance with observations by Akcay et al.[21].

The specificity of the immunostaining was validated by the absence of immunoreaction in kidneys from IL-33-deficient mice. IL-33 was constitutively expressed in both peritubular and periglomerular cells, predominantly in nuclei (data not shown). No immunofluorescence was detected in IL-33-deficient mice (data not shown). Co-staining of IL-33 and CD31, a highly specific endothelial cell marker, revealed a majority (approximately 60-70%) of interstitial cells co-expressing both molecules (data not shown). The 20-30% CD31(−)IL-33(+) cells were not resident immune cells, as assessed by co-staining with the common leukocyte marker CD45. Indeed, CD45-bright cells identified as leukocytes did not express IL-33 (data not shown).

IRI-Induced IL-33 Release from Peritubular and Periglomerular Endothelial Cells Does Not Require Transcription Tissue injury following kidney ischemia-reperfusion is initiated by acute reduction of blood flow leading to endothelial cell necrosis. We surmised that IL-33 might be released from necrotic endothelial cells soon after ischemia-reperfusion. To test this assumption, we induced IRI in WT C57BL/6 mice by unilateral clamping of the renal pedicle for 32 min after contralateral nephrectomy. IL-33 immunofluorescence staining was clearly diminished in both periglomerular and peritubular endothelial (CD31(+)) cells (data not shown) as soon as one hour after reperfusion of the injured kidneys, as compared to their healthy contralateral (Ctr) counterparts (data not shown) used as internal «steady-state» controls. Consistent with alarmin release, intracellular IL-33 was not decreased in sham-operated (Sham) mice (data not shown), without clamping. This partial early loss of IL-33 from ischemic kidney was confirmed by western-blot analysis (data not shown). It was concomitant with a rise of circulating IL-33, which was virtually undetectable before IRI (T0), but increased in plasma one hour after clamping. A partial, transient but lesser increase took place in Sham mice, (data not shown) at this time point, due to the incision alone. Elevated plasma IL-33 levels persisted for up to 6 hours and returned to baseline within 24 hours of reperfusion (data not shown). Release of IL-33 1 hour post-reperfusion did not require transcription, as attested by RTqPCR analysis, which revealed no difference in 11-33 gene expression between control (Ctr) (1.0±0.035, mean±SEM, n=7) and one-hour post-ischemic (0.95±0.08, mean±SEM, n=5; p=0.67, t-test) kidneys. These data support a release of endogenous protein rather than de novo synthesis soon after injury, in accordance with the notion that IL-33 acts as an alarmin in ischemic mice.

Mice Lacking IL-33 or Its Specific Receptor ST2 are Protected Against IRI

Figure 1C:
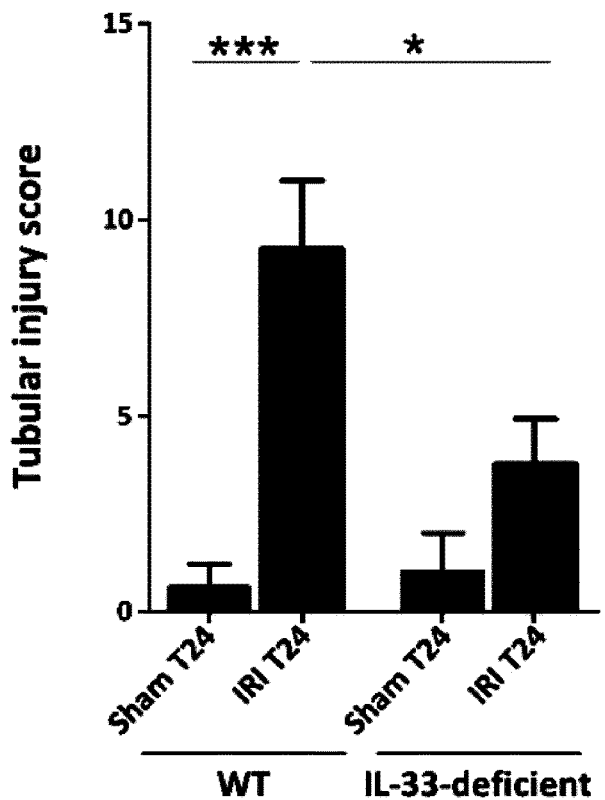

We assessed the effect of IL-33 on kidney functions by measuring blood creatinine (FIG. 1A) and urea nitrogen (BUN) (FIG. 1B), in WT and IL-33-deficient mice 24 hours after clamping. No renal dysfunction was revealed by these criteria in mice lacking IL-33, relative to their Sham counterparts. This result was confirmed by their 100% survival rate within the first 3-4 days after surgery, contrasting with 50% survival in WT mice, as a result of severe renal insufficiency (FIG. 2). Acute tubular necrosis (ATN) assessed by loss of brush border, cast formation, tubular dilatation and inflammatory infiltrates at the cortico-medullary junction was reduced in IL-33-deficient kidneys versus their WT counterparts (data not shown), resulting in significantly lower ATN scores (FIG. 1C). Kidneys from mice deficient for ST2 displayed a similarly moderate ATN score (FIGS. 3A and B), which proves that IL-33 induces kidney IRI via its specific ST2 receptor.

Figure 1D:
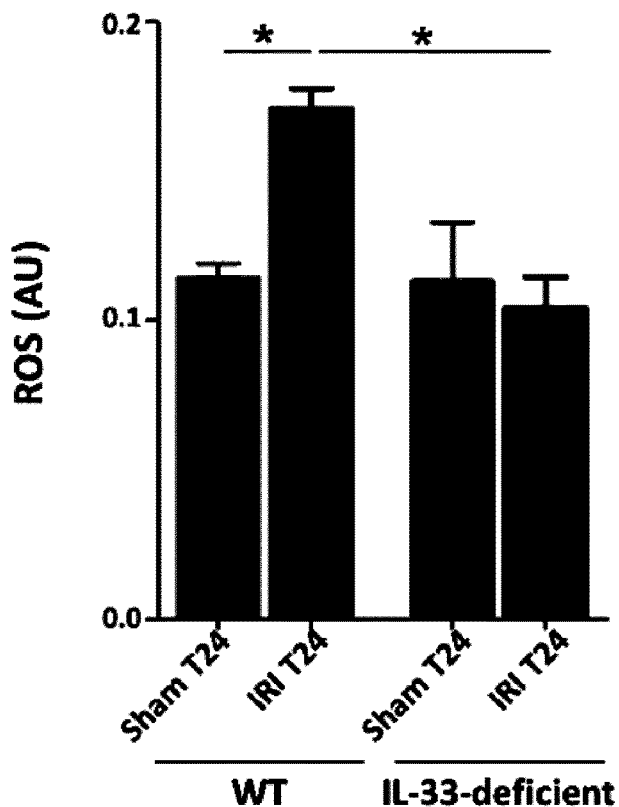

In the ischemic kidney, generation of reactive oxygen species (ROS) at reperfusion initiates a cascade of deleterious cellular responses leading to inflammation, cell death, and acute kidney failure[33,34]. We evaluated the effect of IL-33 deficiency on ROS production by CellROX staining in our renal IRI model (FIG. 1D). In basal conditions, fluorescent staining was weak, as illustrated in Sham kidneys of both WT and IL-33-deficient mice. Following ischemia and subsequent 24-hour reperfusion, ROS production increased in WT mice, but not in their IL-33-deficient counterpart, supporting the hypothesis that IRI severity depends on IL-33. This conclusion was confirmed when considering collagen deposition in ischemic kidneys (FIG. 4), which is also known to depend on IRI severity[35,36].

IL-33 Deficiency Alters Both Post-IRI Trafficking and Pro-Inflammatory Cytokine Expression of Myeloid Cells Following ischemia/reperfusion, neutrophils, monocytes/macrophages and myeloid dendritic cells (DC) are recruited to the kidney, where they mediate IRI[6]. We assessed the contribution of IL-33 to this process by comparing the incidence of total renal leukocytes, identified as CD45(+) cells, in WT and IL-33-deficient mice 24 hours post-IRI. Total CD45(+) cell counts were significantly higher in kidneys undergoing IRI in WT mice than in untreated and Sham mice (data not shown), indicating a marked infiltration. Notably, CD45(+) cell recruitment was reduced at least twice in mice lacking IL-33. Further examination of these cells showed that monocyte/macrophage (CD11b$^{high}$F4/80$^{low}$) (data not shown), myeloid DC (CD11b$^{low}$ F4/80$^{high}$) (data not shown) and neutrophil (GR-1$^{high}$ CD11b$^{high}$) (data not shown) counts were all diminished, reflecting lesser myeloid trafficking.

Previous studies have demonstrated the potential role of IFN-γ- and IL-17A-producing neutrophils in acute renal IRI[31,32]. We analyzed the expression of these two cytokines using intracellular flow cytometry in neutrophils from WT and IL-33-deficient kidneys 24 hours post-IRI. Most infiltrating neutrophils co-expressed IFN-γ and IL-17A in WT kidneys, while this subset was clearly diminished in IL-33-deficient mice. The frequency of IFN-γ(−)/IL-17A(−) neutrophils was accordingly increased in kidneys from IL-33-deficient versus WT counterparts.

Renal iNKT Cell Recruitment, Activation and Cytokine Production are Impaired in IL-33-Deficient Post-IRI Mice Ischemia-reperfusion-induced activation and recruitment of iNKT cells to the kidney are considered critical for neutrophil infiltration and pro-inflammatory cytokine production before kidney injury[6]. Knowing that IL-33 drives iNKT cell activation and recruitment to inflammatory tissues[37], we examined how its deficiency affected this subset 24 hours after IRI induction. As previously reported[31,32], iNKT cells (PBS57-loaded CD1d TT(+) CD3(+)) were markedly increased, in WT kidneys post-IRI compared to untreated and Sham controls, both in terms of cell counts (data not shown) and of frequency (data not shown). Moreover, their CD69 cell surface expression was upregulated (data not shown), reflecting their activation by IRI. In the same conditions, neither increase occurred in mice deficient in IL-33, which established its critical role in IRI-induced iNKT cell trafficking. Plasma levels of IP-10/CXCL10, MIG/CXCL9 and RANTES/CCL5, three chemokines well-recognized for their capacity to recruit iNKT cells at the sites of inflammation[38,39], were increased within 3 hours after IRI induction, but this occurred in a similar manner in WT and IL-33-deficient mice, a finding suggesting that these chemokines do not depend on IL-33 for their production during IRI.

It has been proposed that during IRI, activated iNKT cells promote recruitment and IFN-γ production by neutrophils through the IFN-γ and IL-17A they generate. Consistent with a potential role of endogenous IL-33 in this process, the frequency of IFN-γ(+)/IL-17A(+) T cells tended to decrease in IL-33-deficient mice (data not shown), while IFN-γ/IL-17A expression level in iNKT cells was significantly reduced (data not shown). This corroborates our finding that IL-33 targets iNKT cells to induce both IFN-γ[29,30] and IL-17A production in vitro (data not shown).

As iNKT cells, NK cells, which are also known to be targeted by IL-33[29,30] and recruited during IRI[40], displayed increased recruitment and IFN-γ/IL-17 expression in kidneys from WT mice 24 hours post-IRI, a phenomenon partially lost in their IL-33-deficient counterparts (data not shown).

IRI-Induced Release of IL-33 Promotes Neither Renal Injury Nor Neutrophil Infiltration in Mice Lacking iNKT Cells The key role of IL-33 in mediating iNKT cell activation and recruitment in renal IRI is supported by the similar phenotype of iNKT cell-deficient Jα18KO and IL-33-deficient mice, namely complete protection against IRI (data not shown) together with decreased neutrophil (data not shown) and monocyte/macrophage (data not shown) infiltration. Note that the plasma levels and time course of IL-33 release into peripheral blood were not affected by iNKT cell deficiency in Jα18KO mice undergoing IRI (data not shown), a finding which highlights the requirement of iNKT cells as mediator of IL-33 activity.

Initial IRI-Induced Kidney Lesions But Not Concomitant Myeloid Recruitment Depend on IL-33.

The peak of the IL-33-dependent inflammatory response 24 hours after IRI induction was preceded by a very early phase, comprising the first 6 hours of reperfusion, characterized by a slight but significant increase of creatinine/BUN levels and ATN scores (data not shown), and myeloid cell infiltration (data not shown). The fact that both tubular epithelial necrosis and alterations of kidney functions but neither myeloid cell recruitment (data not shown) nor the increase in chemokines MCP-1/CCL2 and MIP-2/CXCL2 (data not shown) responsible for their recruitment to inflammatory sites[41] were lost in 6 hours post-IRI IL-33-deficient mice supports the notion that IL-33 initiates tissue lesions in an immune cell-independent fashion. This evidence corroborates our finding in vitro that IL-33 targets renal epithelial cells (data not shown). Moreover, this initial inflammatory episode preceded the recruitment of iNKT cells (data not shown), NK cells and myeloid DC (data not shown), which indicates that the IL-33/innate ST2-expressing cell axis amplifies rather than initiates monocyte/macrophage and neutrophil infiltration.

Increase of Circulating IL-12 and Surface ST2 Over-Expression on iNKT Cells Precede the IL-33-Dependent Phase of Innate Immune Cell Infiltration Intriguingly, even though IL-33 release reached its peak as soon as 1 hour post-IRI, its effect on myeloid cell recruitment occurred only 24 hours after IRI induction. A probable explanation is that IL-33 targets iNKT cells as a cofactor of TCR and/or IL-12 stimulation rather than an independent stimulus. Indeed, we noted a three-fold increase of plasma IL-12, which reached its peak only 6 hours post-IR (data not shown). Just like IL-12 release, it was reported that TCR-mediated activation of iNKT cells does not occur within the first hours following induction of IRI[31], while IL-33 dramatically enhances IFN-g production by iNKT cells stimulated upon TCR in combination with IL-12 ([28-30] and data not shown). These data together with the fact that maximal increase of surface ST2 levels on iNKT cells was not achieved within the first hours after clamping (data not shown) may explain why an amplification effect of IL-33 on immune cells was manifested only 24 hours post-IRI.

Discussion:

Endogenous IL-33 has been identified as an alarmin mediating danger signals during tissue damage[16]. This concept has recently been applied to human kidney transplantation, in which renal injury is associated with early IL-33 release[28]. It is also relevant to in vitro hypoxia/re-oxygenation of endothelial cell, which mimics in vivo conditions post-IRI[28].

We demonstrate here for the first time that endogenous IL-33, released from endothelial cells as alarmin, contributes to the pathogenesis of IRI-induced kidney injury by targeting both immune and non-immune cells. Without IL-33, clinical and histological hallmarks of acute ischemic renal failure were attenuated, with less severe tubulo-interstitial injury and preserved renal function.

IL-33 is mainly and constitutively expressed in the nuclei of epithelial barrier tissues and endothelial cells, and can therefore be immediately released in response to cell injury. The few studies on the cellular localization of IL-33 in the kidney have documented a constitutive expression in endothelial nuclei of renal large and small vessels in humans[42], and also in peritubular vascular endothelial cells with a similar expression profile[21,23] in mice. In agreement with these data, we demonstrate here that in healthy murine kidneys IL-33 is mainly expressed by (CD31(+)CD45(−)) endothelial cells in peritubular capillaries and by CD31(−) CD45(−) interstitial cells, which may be pericytes, endothelial progenitor cells and/or fibroblasts.

The initial event triggering tissue injury after kidney ischemia-reperfusion is acute reduction of blood flow followed by endothelial cell necrosis. We found that full-length active IL-33 disappeared from renal endothelial cells and increased in circulation within only 1 hour of reperfusion, with no change in Il-33 mRNA expression. This result proves that in this situation IL-33 can signal damage as an alarmin, once released from the nucleus of dying endothelial cells.

As an immediate result, IL-33 initiates renal lesions in an immune cell-independent fashion, presumably by direct targeting of tubular epithelial cells. These data, even though it remains to be determined whether IL-33 has cytotoxic activity on renal proximal tubule epithelial cells, are consistent with the F Molitoris group's view that endothelial injury is the initial event in renal IRI[43].

In addition, IL-33 further amplifies tissue injury, especially involving neutrophils via its effect on iNKT lymphocytes, whose deleterious action during kidney IRI is widely recognized. Indeed, following ischemia-reperfusion, neutrophils are recruited to the kidney, where they act as major IRI effector cells[44-46]. It is widely acknowledged that their recruitment and activation depend on iNKT cells, presumably via their IFN-γ/IL-17A production[31,32]. We provide three lines of evidence that IL-33 and iNKT cells interact directly to promote neutrophil infiltration in ischemic kidneys: (i) iNKT cells constitutively express the IL-33 receptor-specific ST2 chain[29,30]; (ii) IL-33 drives recruitment of iNKT cells, and induces their IFN-γ/IL-17A production in response to ischemia-reperfusion, and (iii) IL-33, iNKT cells, and IFN-γ/IL-17A production are interconnected, since recombinant IL-33 targets iNKT cells in vitro to induce the pro-inflammatory cytokines that mediate IRI. Like iNKT cells, neutrophils express ST2 and could therefore respond directly to IL-33. However, the failure to recruit neutrophils in mice lacking iNKT cells does not support this assumption.

At steady state[29] and in patho-physiological settings[37], IL-33 seems to behave like a cofactor of IL-12 and/or TCR stimulation rather than as an independent stimulus by targeting iNKT cells. Consistent with a similar scenario during IRI, we noted an increase of plasma IL-12, while Marques et al.[47] reported protection of IL-12-deficient mice. Moreover, recruitment/activation of iNKT cells during IRI is mediated through interactions with CD1d[31,32], implying that endogenous Ags, presumably self-glycolipids associated with CD1d molecules and recognized by the invariant TCR, are involved[48]. These lines of evidence together with our demonstration that myeloid DC recruitment during IRI depends on IL-33, raise the possibility that the DC compartment concomitantly releases IL-12 and presents iNKT cell ligands during IRI, as reported in response to stress conditions[48-51].

Together with our evidence for a direct interaction of IL-33 with iNKT cells to regulate non-infectious inflammation in the lung[37], our current study supports the notion that the IL-33/iNKT cell axis represents a new general physiopathological mechanism involved in «sterile inflammation» associated with tissue damage. It may also apply to IRI occurring during human renal transplantation, as suggested by our recent pilot study, which indicates that prompt release of IL-33 into the circulation could be responsible for the early activation of iNKT lymphocytes[28]. This study and another recent study[27] raise the question of whether IL-33 released into the blood could be an early AKI biomarker in humans.

Our current study improves understanding of the role of IL-33 as an alarmin during kidney IR, especially the underlying mechanisms of its implication in the dynamic between renal endothelial and epithelial cells. Moreover, the alarmin signaling pathway may become instrumental as a new therapeutic target, through which the innate inflammatory cascade involved in IRI and AKI could be neutralized. This approach would be beneficial for long-term graft survival, which represents a major challenge in transplantation.

REFERENCES

Throughout this application, various references describe the state of the art to which this invention pertains. The disclosures of these references are hereby incorporated by reference into the present disclosure.

1. Nankivell B J, Chapman J R: Chronic allograft nephropathy: current concepts and future directions. *Transplantation* 81: 643-654, 2006
2. Malek M, Nematbakhsh M: Renal ischemia/reperfusion injury; from pathophysiology to treatment. *J. Ren. Inj. Prev.* 4: 20-27, 2015
3. Venkatachalam M A, Griffin K A, Lan R, Geng H, Saikumar P, Bidani A K: Acute kidney injury: a springboard for progression in chronic kidney disease. *Am. J. Physiol. Renal Physiol.* 298: F1078-1094, 2010
4. Eltzschig H K, Eckle T: Ischemia and reperfusion—from mechanism to translation. *Nat. Med.* 17: 1391-1401, 2011
5. Thurman J M: Triggers of inflammation after renal ischemia/reperfusion. *Clin. Immunol. Orlando Fla* 123: 7-13, 2007
6. Jang H R, Rabb H: Immune cells in experimental acute kidney injury. *Nat. Rev. Nephrol.* 11: 88-101, 2015
7. Li J, Gong Q, Zhong S, Wang L, Guo H, Xiang Y, Ichim T E, Wang C-Y, Chen S, Gong F, Chen G: Neutralization of the extracellular HMGB1 released by ischaemic damaged renal cells protects against renal ischaemia-reperfusion injury. *Nephrol. Dial. Transplant. Off Publ. Eur. Dial. Transpl. Assoc.—Eur. Ren. Assoc.* 26: 469-478, 2011
8. Zhang J, Xia J, Zhang Y, Xiao F, Wang J, Gao H, Liu Y, Rong S, Yao Y, Xu G, Li J: HMGB1-TLR4 signaling participates in renal ischemia reperfusion injury and could be attenuated by dexamethasone-mediated inhibition of the ERK/NF-κB pathway. *Am. J. Transl. Res.* 8: 4054-4067, 2016
9. Matzinger P: Tolerance, danger, and the extended family. *Annu. Rev. Immunol.* 12: 991-1045, 1994
10. Matzinger P: The danger model: a renewed sense of self. *Science* 296: 301-305, 2002
11. Tsung A, Klune J R, Zhang X, Jeyabalan G, Cao Z, Peng X, Stolz D B, Geller D A, Rosengart M R, Billiar T R: HMGB1 release induced by liver ischemia involves Toll-like receptor 4 dependent reactive oxygen species production and calcium-mediated signaling. *J. Exp. Med.* 204: 2913-2923, 2007

12. Kono H, Chen C-J, Ontiveros F, Rock K L: Uric acid promotes an acute inflammatory response to sterile cell death in mice. *J. Clin. Invest.* 120: 1939-1949, 2010
13. Oppenheim J J, Yang D. Alarmins: chemotactic activators of immune responses. *Curr Opin Immunol.* 17:359-65, 2005
14. Ali S, Huber M, Kollewe C, Bischoff S C, Falk W, Martin M U: IL-1 receptor accessory protein is essential for IL-33-induced activation of T lymphocytes and mast cells. *Proc. Natl. Acad. Sci. U.S.A.* 104: 18660-18665, 2007
15. Schmitz J, Owyang A, Oldham E, Song Y, Murphy E, McClanahan T K, Zurawski G, Moshrefi M, Qin J, Li X, Gorman D M, Bazan J F, Kastelein R A: IL-33, an interleukin-1-like cytokine that signals via the IL-1 receptor-related protein ST2 and induces T helper type 2-associated cytokines. *Immunity* 23: 479-490, 2005
16. Moussion C, Ortega N, Girard J-P: The IL-1-like cytokine IL-33 is constitutively expressed in the nucleus of endothelial cells and epithelial cells in vivo: a novel "alarmin"? *PloS One* 3: e3331, 2008
17. Haraldsen G, Balogh J, Pollheimer J, Sponheim J, Küchler A M: Interleukin-33—cytokine of dual function or novel alarmin? *Trends Immunol.* 30: 227-233, 2009
18. Lamkanfi M, Dixit VM: IL-33 raises alarm. *Immunity* 31: 5-7, 2009
19. Liew F Y, Girard J-P, Turnquist H R: Interleukin-33 in health and disease. *Nat. Rev. Immunol.* 16: 676-689, 2016
20. Baekkevold E S, Roussigné M, Yamanaka T, Johansen F-E, Jahnsen F L, Amalric F, Brandtzaeg P, Erard M, Haraldsen G, Girard J-P: Molecular characterization of NF-HEV, a nuclear factor preferentially expressed in human high endothelial venules. *Am. J. Pathol.* 163: 69-79, 2003
21. Akcay A, Nguyen Q, He Z, Turkmen K, Lee D W, Hernando AA, Altmann C, Toker A, Pacic A, Ljubanovic D G, Jani A, Faubel S, Edelstein C L: IL-33 Exacerbates Acute Kidney Injury. *J. Am. Soc. Nephrol.* 22: 2057-2067, 2011
22. Gadani S P, Walsh J T, Smirnov I, Zheng J, Kipnis J: The glia-derived alarmin IL-33 orchestrates the immune response and promotes recovery following CNS injury. *Neuron* 85: 703-709, 2015
23. Chen W-Y, Chang Y-J, Su C-H, Tsai T-H, Chen S-D, Hsing C-H, Yang J-L: Upregulation of Interleukin-33 in obstructive renal injury. *Biochem. Biophys. Res. Commun.* 473: 1026-1032, 2016
24. Riedel J H, Becker M, Kopp K, Düster M, Brix S R, atherine Meyer-Schwesinger C, Kluth La, Gnirck A C, Attar M, Krohn S, Boris Fehse B, Stahl R. A. K, Panzer U and Turner J E: IL-33-Mediated Expansion of Type 2 Innate Lymphoid Cells Protects from Progressive Glomerulosclerosis. *J. Am. Soc. Nephrol.* 28 (7) 2068-2080, 2017
25. Stremska M E, Jose S, Sabapathy V, Huang L, Bajwa A, Kinsey G R, Sharma P R, Mohammad S, Rosin D L, Okusa M D, Sharma R: IL-233, A Novel IL-2 and IL-33 Hybrid Cytokine, Ameliorates Renal Injury. *J. Am. Soc. Nephrol.* 28(9):2681-2693, 2017
26. Bao Y-S, Na S-P, Zhang P, Jia X-B, Liu R-C, Yu C-Y, Mu S-H, Xie R-J: Characterization of interleukin-33 and soluble ST2 in serum and their association with disease severity in patients with chronic kidney disease. *J. Clin. Immunol.* 32: 587-594, 2012
27. Ravichandran K, Holditch S, Brown C N, Wang Q, Ozkok A, Weiser-Evans M C, Nemenoff R A, Miyazaki M, Thiessen-Philbrook H, Parikh C R, Ljubanovic D, Edelstein C L. IL-33 deficiency slows cancer growth but does not protect against cisplatin-induced AKI in mice with cancer. *Am J Physiol Renal Physiol.* doi: 10.1152/ajprenal.00040.2017
28. Thierry A, Giraud S, Robin A, Barra A, Bridoux F, Ameteau V, Hauet T, Girard J-P, Touchard G, Gombert J-M, Herbelin A: The alarmin concept applied to human renal transplantation: evidence for a differential implication of HMGB1 and IL-33. *PloS One* 9: e88742, 2014
29. Bourgeois E, Van L P, Samson M, Diem S, Barra A, Roga S, Gombert J-M, Schneider E, Dy M, Gourdy P, Girard J-P, Herbelin A: The pro-Th2 cytokine IL-33 directly interacts with invariant NKT and NK cells to induce IFN-gamma production. *Eur. J. Immunol.* 39: 1046-1055, 2009
30. Smithgall M D, Comeau M R, Yoon B-RP, Kaufman D, Armitage R, Smith D E: IL-33 amplifies both Th1- and Th2-type responses through its activity on human basophils, allergen-reactive Th2 cells, iNKT and NK cells. *Int. Immunol.* 20: 1019-1030, 2008
31. Li L, Huang L, Sung S J, Lobo P I, Brown M G, Gregg R K, Engelhard V H, Okusa M D: NKT cell activation mediates neutrophil IFN-gamma production and renal ischemia-reperfusion injury. *J. Immunol. Baltim. Md* 1950 178: 5899-5911, 2007
32. Li L, Huang L, Vergis A L, Ye H, Bajwa A, Narayan V, Strieter R M, Rosin D L, Okusa M D: IL-17 produced by neutrophils regulates IFN-gamma-mediated neutrophil migration in mouse kidney ischemia-reperfusion injury. *J. Clin. Invest.* 120: 331-342, 2010
33. Baud L, Ardaillou R: Involvement of reactive oxygen species in kidney damage. *Br. Med. Bull.* 49: 621-629, 1993
34. Sharfuddin A A, Molitoris B A: Pathophysiology of ischemic acute kidney injury. *Nat. Rev. Nephrol.* 7: 189-200, 2011
35. Duffield J S: Cellular and molecular mechanisms in kidney fibrosis. *J. Clin. Invest.* 124: 2299-2306, 2014
36. Hueper K, Gutberlet M, Rong S, Hartung D, Mengel M, Lu X, Haller H, Wacker F, Meier M, Gueler F: Acute kidney injury: arterial spin labeling to monitor renal perfusion impairment in mice-comparison with histopathologic results and renal function. *Radiology* 270: 117-124, 2014
37. Bourgeois E A, Levescot A, Diem S, Chauvineau A, Berges H, Milpied P, Lehuen A, Damotte D, Gombert J-M, Schneider E, Girard J-P, Gourdy P, Herbelin A: A natural protective function of invariant NKT cells in a mouse model of innate-cell-driven lung inflammation. *Eur. J. Immunol.* 41: 299-305, 2011
38. Farber J M: Mig and IP-10: CXC chemokines that target lymphocytes. *J. Leukoc. Biol.* 61: 246-257, 1997
39. Marra F, Tacke F: Roles for chemokines in liver disease. *Gastroenterology* 147: 577-594.e1, 2014
40. Zhang Z-X, Wang S, Huang X, Min W-P, Sun H, Liu W, Garcia B, Jevnikar A M: NK cells induce apoptosis in tubular epithelial cells and contribute to renal ischemia-reperfusion injury. *J. Immunol. Baltim. Md* 1950 181: 7489-7498, 2008
41. Chung A C K, Lan H Y: Chemokines in Renal Injury. *J. Am. Soc. Nephrol.* 22: 802-809, 2011
42. Chen W-Y, Li L-C, Yang J-L: Emerging Roles of IL-33/ST2 Axis in Renal Diseases. *Int. J. Mol. Sci.* 18: 2017

43. Molitoris B A, Sutton T A: Endothelial injury and dysfunction: role in the extension phase of acute renal failure. *Kidney Int.* 66: 496-499, 2004
44. Bolisetty S and Agarwal A: Neutrophils in acute kidney injury: not neutral any more. *Kidney Int.* 75(7): 674-6, 2009
45. Awad A S , Rouse M , Huang L et al. Compartmentalization of neutrophils in the kidney and lung following acute ischemic kidney injury. *Kidney Int.* 75: 689-698, 2009
46. Tanaka S, Tanaka T, Kawakami T, Takano H, Sugahara M, Saito H, Higashijima Y, Yamaguchi J, Inagi R, Nangaku M: Vascular adhesion protein-1 enhances neutrophil infiltration by generation of hydrogen peroxide in renal ischemia/reperfusion injury. *Kidney Int.* S0085-2538(17)30041-8, 2017
47. Marques V P, Gonçalves G M, Feitoza C Q, Cenedeze M A, Fernandes Bertocchi A P, Damião M J, Pinheiro H S, Antunes Teixeira V P, dos Reis M A, Pacheco-Silva A, Saraiva Câmara N O: Influence of TH1/TH2 switched immune response on renal ischemia-reperfusion injury. *Nephron Exp. Nephrol.* 104: e48-56, 2006
48. Bendelac A, Savage P B, Teyton L: The biology of NKT cells. *Annu. Rev. Immunol.* 25: 297-336, 2007
49. Kitamura H, Iwakabe K, Yahata T, Nishimura S, Ohta A, Ohmi Y, Sato M, Takeda K, Okumura K, Van Kaer L, Kawano T, Taniguchi M, Nishimura T: The natural killer T (NKT) cell ligand alpha-galactosylceramide demonstrates its immunopotentiating effect by inducing interleukin (IL)-12 production by dendritic cells and IL-12 receptor expression on NKT cells. *J Exp Med.* 189(7):1121-8, 1999.
50. Vincent M S, Leslie D S, Gumperz J E, Xiong X, Grant E P, Brenner M B: CD1-dependent dendritic cell instruction. *Nat Immunol.* 3 (12):1163-8, 2002
51. Brigl M, Bry L, Kent S C, Gumperz J E, Brenner M B: Mechanism of CD1d-restricted natural killer T cell activation during microbial infection. *Nat. Immunol.* 4: 1230-1237, 2003
52. Pichery M, Mirey E, Mercier P, Lefrancais E, Dujardin A, Ortega N, Girard J-P: Endogenous IL-33 is highly expressed in mouse epithelial barrier tissues, lymphoid organs, brain, embryos, and inflamed tissues: in situ analysis using a novel Il-33-LacZ gene trap reporter strain. *J. Immunol. Baltim. Md 1950* 188: 3488-3495, 2012
53. Cui J, Shin T, Kawano T, Sato H, Kondo E, Toura I, Kaneko Y, Koseki H, Kanno M, Taniguchi M: Requirement for Valpha14 NKT cells in IL-12-mediated rejection of tumors. *Science* 278: 1623-1626, 1997
54. Townsend M J, Fallon P G, Matthews D J, John H E, McKenzie A N: T1/ST2-deficient mice demonstrate the importance of T1/ST2 in developing primary T helper cell type 2 responses. *J. Exp. Med.* 191: 1069-1076, 2000
55. Xue G P, Fishlock R C, Snoswell A M: Determination of creatinine in whole blood, plasma, and urine by high-performance liquid chromatography. *Anal. Biochem.* 171(1):135-40, 1988

The invention claimed is:

1. A method of preventing, reducing the severity of, or reducing the risk of ischemia reperfusion injury (IRI) caused by reperfusion of an organ or tissue comprising
administering to the organ or tissue a therapeutically effective amount of an interleukin-33 (IL-33) antagonist, wherein:
the IL-33 antagonist is an antibody having binding affinity for IL-33,
the step of administering occurs before and/or during the reperfusion of the organ or tissue,
the IRI includes one or both of severe renal insufficiency and acute tubular necrosis.

2. The method of claim 1, wherein the IL-33 antagonist is administered directly into a subject or directly into an isolated organ using injection, a pump device and/or a bypass machine.

3. The method of claim 1, further comprising measuring plasma creatinine and blood urea nitrogen (BUN) post-reperfusion to assess renal function.

4. The method of claim 1, wherein the IL-33 antagonist is administered before reperfusion of the organ or tissue.

5. The method of claim 1, wherein the IL-33 antagonist is administered during reperfusion of the organ or tissue.

6. A method for preventing progression to chronic kidney disease (CKD) after an acute kidney injury (AKI) in a subject in need thereof, comprising administering to the subject a therapeutically effective amount of an interleukin-33 (IL-33) antagonist, wherein the IL-33 antagonist is an antibody having binding affinity for IL-33 or an antibody having binding affinity for an extracellular domain of ST2,
wherein the AKI is caused by at least one condition selected from the group consisting of ischemia, ischemia reperfusion injury (IRI), malignant hypertension, hemolytic uremic syndrome, thrombotic thrombocytopeniaurpura, hypersensitivity angiitis, serum sickness, Wegener's granulomatosis, giant cell arteritis, Henoch-Schonlein purpura, a post-infectious abnormality, rapidly progressive glomerulonephritis, membranoproliferative glomerulonephritis, Goodpasture's syndrome, papillary necrosis, lymphoma, intratubular obstruction from crystal deposition, light chain disease, hemorrhage, hypotension, burns, renal infarction, renal artery dissection, rhabdomyolysis, trauma, transfusion reactions, myoglobinemia, heat stroke, snake bite and spider bite,
and wherein if the AKI is caused by IRI of an organ or tissue, the IL-33 antagonist is administered before and/or during reperfusion of the organ or tissue, and the IRI includes one or both of severe renal insufficiency and acute tubular necrosis.

7. The method of claim 6, wherein the at least one condition is ischemia or ischemia reperfusion injury.

* * * * *